(12) United States Patent
Mirkin et al.

(10) Patent No.: US 6,726,847 B2
(45) Date of Patent: Apr. 27, 2004

(54) SILVER STAIN REMOVAL BY CHEMICAL ETCHING AND SONICATION

(75) Inventors: Chad A. Mirkin, Wilmette, IL (US); So-Jung Park, Evanston, IL (US); Rongchao Jin, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/998,936

(22) Filed: Nov. 30, 2001

(65) Prior Publication Data

US 2002/0125214 A1 Sep. 12, 2002

Related U.S. Application Data

(60) Provisional application No. 60/251,715, filed on Dec. 6, 2000.

(51) Int. Cl.[7] .................................................. C23F 1/00
(52) U.S. Cl. .......................... 216/90; 216/91; 216/92; 216/100; 134/1
(58) Field of Search .......................... 216/90–92, 100; 134/1, 2; 438/906

(56) References Cited

U.S. PATENT DOCUMENTS

| | | | | |
|---|---|---|---|---|
| 4,996,143 A | | 2/1991 | Heller et al. ................... | 435/6 |
| 5,294,291 A | * | 3/1994 | Akahoshi et al. ............. | 216/12 |
| 5,508,164 A | | 4/1996 | Kausch et al. ................. | 435/6 |
| 5,567,585 A | | 10/1996 | Caetano-Anolles et al. .... | 435/6 |
| 5,922,537 A | | 7/1999 | Ewart et al. .................... | 435/6 |
| 5,972,615 A | | 10/1999 | An et al. ......................... | 435/6 |
| 6,127,122 A | | 10/2000 | Park et al. ....................... | 435/6 |
| 6,214,560 B1 | | 4/2001 | Yguerabide et al. ......... | 435/7.1 |
| 6,264,825 B1 | | 7/2001 | Blackburn et al. ....... | 205/777.5 |
| 6,348,159 B1 | * | 2/2002 | Dapkus et al. ................ | 216/83 |

FOREIGN PATENT DOCUMENTS

| | | |
|---|---|---|
| JP | 52 078633 | 7/1977 |
| JP | 59 089399 | 5/1984 |
| JP | 03 094072 | 4/1991 |
| JP | 04 333504 | 4/1993 |
| JP | 08 103738 | 4/1996 |
| WO | WO 94/29484 | 12/1994 |
| WO | WO 98/04740 | 2/1998 |
| WO | WO 99/23258 | 5/1999 |
| WO | WO 00/25136 | 5/2000 |
| WO | WO 00/33079 | 6/2000 |

OTHER PUBLICATIONS

Mohanty J., et al. "Pulsed laser excitation of phosphate stabilized silver nanoparticles," *Proc. Indian Acd. Sci.*, vol. 112, No. 1, p. 63–72, Feb. 2000.

Nicewarner–Peña S., et al., "Hybridization and Enzymatic Extension of Au Nanoparticle–Bound Oligonucleotides," *J. Am. Chem. Soc.*, vol. 124, p. 7314–7323 (2002).

Whitesides G.M., et al., "Soft Lithography in Biology and Biochemistry," *Annu. Rev. Biomed. Eng.*, p. 335–373 (2001).

Bassell, et al., Single mRNA's Visualized by Ultrastructural in Situ Hybridization Are Principally Localized at Actin Filament Intersections in Fibroblasts, *The Journal of Cell Biology*, vol. 126, No. 4, p. 863–876 (1994).

Braun, et al., DNA–templated assembly and electrode attachment of a conducting silver wire, *Nature*, vol. 391, p. 775–778, (1998).

Braun–Howland, et al., Development of a Rapid Method for Detecting Bacterial Cell In Situ Using 16S rRNA–Targeted Probes, *Biotechniques*, vol. 13, No. 6, p. 928–931, (1992).

T.A. Taton, et al., Scanometric DNA Array Detection with Nanoparticle Probes, *Science*, vol. 289, p. 1757–1760 (2000).

Xia, et al., A Selective Etching Solution for Use with Patterned Self–Assembled Monolayers of Alkanethiolates on Gold, *Chem. Mater.*, 1995, 7, p. 2332–2337.

* cited by examiner

*Primary Examiner*—Anita Alanko
(74) *Attorney, Agent, or Firm*—McDonnell Boehnen Hulbert & Berghoff LLP

(57) ABSTRACT

This invention relates to methods for regenerating spent DNA detection chips for further use. Specifically, this invention relates to a method for removal of silver from used DNA detection chips that employ gold nanoparticle-oligonucleotide conjugate probes and that use silver staining for signal amplification.

16 Claims, 1 Drawing Sheet

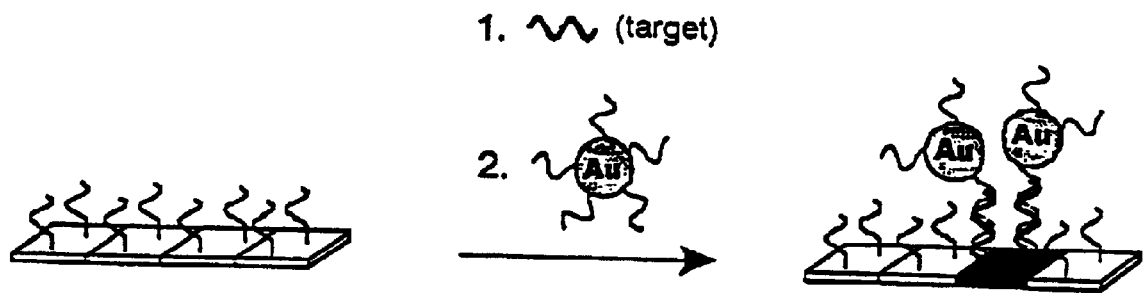
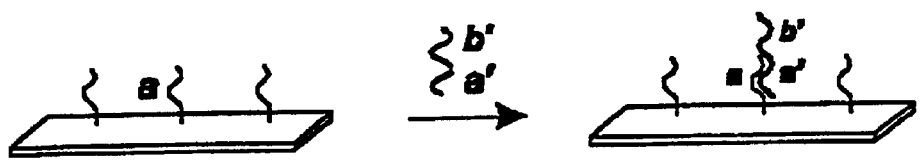
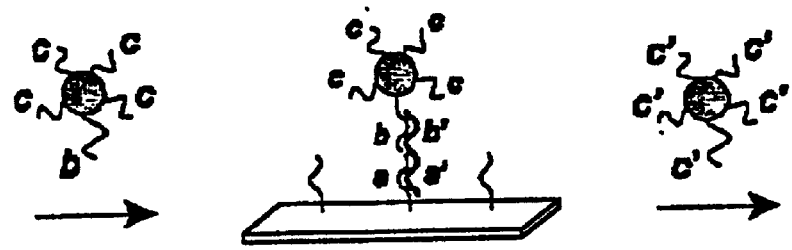
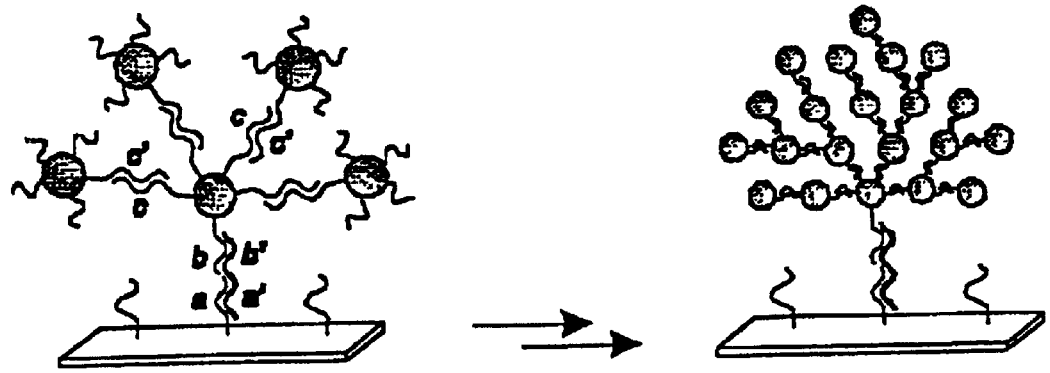
Figure 2

SILVER STAIN REMOVAL BY CHEMICAL ETCHING AND SONICATION

This application claims priority to U.S. provisional patent application Ser. No. 60/251,715, filed Dec. 6, 2000.

FIELD OF THE INVENTION

The present invention relates to method for regenerating spent DNA detection chips for further use. More specifically, the present invention relates to a method for the removal of silver from used DNA detection chips that employ gold nanoparticle-oligonucleotide conjugate probes and that use silver staining for signal amplification.

BACKGROUND OF THE INVENTION

Sequence-selective DNA detection has become increasingly important as scientists unravel the genetic basis of disease and use this new information to improve medical diagnosis and treatment. DNA hybridization tests on oligonucleotide-modified substrates are commonly used to detect the presence of specific DNA sequences in solution. The developing promise of combinatorial DNA arrays for probing genetic information illustrates the importance of these heterogeneous sequence assays to future science. In most assays, the hybridization of fluorophore-labeled targets to surface bound probes is monitored by fluoresecence microscopy or densitometry. Although fluoresence detection is very sensitive, its use is limited by the expense of the experimental equipment and by background emissions from most common substrates. In addition, the selectivity of labeled oligonucleotide targets for perfectly complementary probes over those with single base mismatches is poor, preventing the use of surface hybridization tests for detection of single nucleotide polymorphisms. A detection scheme which improved upon the simplicity, sensitivity and selectivity of fluorescent methods could allow the full potential of combinatorial sequence analysis to be realized.

One such technique is the chip based DNA detection method that employs gold nanoparticle probes, modified with oligonucleotides, to indicate the presence of a particular DNA sequence hybridized on a transparent substrate in a three component sandwich assay format. See T. A. Taton, C. A. Mirkin, R. L. Letsinger, *Science,* 289, 1757 (2000). For low target DNA concentrations, the method employs nanoparticle-promoted silver reduction for signal amplification. The amplification step increases the sensitivity of the chip and provides for facile DNA detection. However, the silver cannot be readily removed from the chip by simply washing with water to reuse the chip as one can do with conventional fluorescence-based arrays. Accordingly, a method and composition for regenerating silver stained DNA nanoparticle-based chips for reuse is desirable.

BRIEF DESCRIPTION OF THE INVENTION

The present invention relates to compositions and methods for the removal of the silver from used DNA detection chips that employ silver staining for signal amplification. The invention relates to chemical compositions, methods using the chemical compositions and sonication methods for removing the silver.

Typically, a plurality of nanoparticle-oligonucleotide conjugates or oligonucletides can be attached to the substrate in an array for detecting multiple portions of a target nucleic acid, for detecting multiple different nucleic acids, or both. For instance, a substrate may be provided with rows of spots, each spot containing a different type of oligonucleotide or oligonucleotide-nanoparticle conjugate designed to bind to a portion of a target nucleic acid. A sample containing one or more nucleic acids is applied to each spot, and the rest of the assay is performed in one of the ways described above using appropriate oligonucleotide-nanoparticle conjugates, oligonucleotide-liposome conjugates, aggregate probes, core probes, and binding oligonucleotides such as the ones described in WO 98/04740, published Feb. 5, 1998 and WO 00/33079, published Jun. 8, 2000.

When a substrate is employed, a detectable change can be produced or further enhanced by silver staining. Silver staining can be employed with any type of nanoparticles that catalyze the reduction of silver. Preferred are nanoparticles made of noble metals (e.g., gold and silver). See Bassell, et al., *J. Cell. Biol.,* 126, 863–876 (1994); Braun-Howland et al., *Biotechniques,* 13, 928–931 (1992). If the nanoparticles being employed for the detection of a nucleic acid do not catalyze the reduction of silver, then silver ions can be complexed to the nucleic acid to catalyze the reduction. See Braun et al., *Nature,* 391, 775 (1998). Also, silver stains are known which can react with the phosphate groups on nucleic acids.

Silver staining can be used to produce or enhance a detectable change in any assay performed on a substrate. In particular, silver staining has been found to provide a huge increase in sensitivity for assays employing a single type of nanoparticle, such as the one illustrated in FIG. 1, so that the use of layers of nanoparticles, aggregate probes and core probes can often be eliminated.

In assays for detecting nucleic acids performed on a substrate, the detectable change can be observed with an optical scanner. Suitable scanners include those used to scan documents into a computer which are capable of operating in the reflective mode (e.g., a flatbed scanner), other devices capable of performing this function or which utilize the same types of optics, any type of grayscale-sensitive measurement device, and standard scanners which have been modified to scan substrates according to the invention (e.g., a flatbed scanner modified to include a holder for the substrate). The resolution of the scanner must be sufficient so that the reaction area on the substrate is larger than a single pixel of the scanner. The scanner can be used with any substrate, provided that the detectable change produced by the assay can be observed against the substrate (e.g., a gray spot, such as that produced by silver staining, can be observed against a white background, but cannot be observed against a gray background). The scanner can be a black and white scanner or a color scanner.

A problem associated with the silver enhancement technique is that the silver cannot be simply removed from the combinatorial DNA array substrates or chips that use oligonucleotide-modified gold nanoparticle probes and that employ nanoparticle-promoted silver reduction for signal amplication.

Accordingly, one object of the invention is to provide compositions for the removal of the silver from DNA detection chip, thereby allowing the chip to be recycled and reused.

Another object of the invention is to provide a cyanide-based method for removing silver from the used DNA detection chip allowing for the recycle and reuse of the chip.

Still another object of the invention is to provide a sonication method for the removal of silver and gold nanoparticles from a used DNA detection chip, thus allowing the chip to be recycled and reused.

DESCRIPTION OF THE DRAWINGS

FIG. 1 illustrates the hybridization of a single type of oligonucleotide-modified gold nanoparticle detection probes, unmodified DNA target, and oligonucleotide capture probes attached to a glass substrate in a three component hybridization sandwich assay.

FIG. 2 illustrates the hybridization of two types of nanoparticle detection probes, unmodified DNA target, and oligonucleotide capture probes attached to a glass substrate in a three component hybridization sandwich assay. The nanoparticle detection probes form a tree of nanoparticles which can be observed with the naked eye.

DETAILED DESCRIPTION OF THE INVENTION

Oligonucleotide-modified gold nanoparticles and unmodified DNA target can be hybridized to oligonucleotide probes attached to a glass substrate in a three component sandwich assay (see FIGS. 1 and 2). The nanoparticles can either be individual ones (see FIG. 1) or "trees" of nanoparticles (see FIG. 2). The "trees" increase signal sensitivity as compared to the individual nanoparticles, and the hybridized gold nanoparticles "trees" often can be observed with the naked eye as dark areas on the glass substrate. When "trees" are not used, or to amplify the signal produced by the trees," the hybridized gold nanoparticles can be treated with a silver staining solution. The "trees" accelerate the staining process, making detection of target nucleic acid faster as compared to individual nanoparticles.

A limit to the silver enhancement technique is that the detection chips that employ nanoparticle-promoted silver reduction cannot be recycled because of the difficulty of removing the silver from the chip surface. Accordingly, the present invention provides compositions and methods for the removal of silver from a used DNA detection chip thus allowing for the recycling and reuse of the chip.

The silver is removed from a used silver stained DNA detection chip by dipping the chip in an etching solution. Any etching solution that can remove silver without destroying the oligonucleotide attachments from the support will work. Examples of aqueous solutions that can be used include a KCN solution containing between about 0.1 moles and about 2 moles of KOH per liter of water, preferably about 1 mole per liter of water; and between about 0.05 moles and about 0.5 moles of KCN per liter of water, preferably about 0.1 moles per liter of water. Another example is an aqueous solution that contains between about 0.01 moles and about 0.5 moles of $Na_2S_2O_3$ per liter of water, preferably about 0.1 moles per liter of water; between about 0.1 moles and about 2 moles of KOH per liter of water, preferably about 1 mole per liter of water; between about 0.001 moles and about 0.1 moles of $K_3FeCN_6$ per liter of water, preferably about 0.01 moles per liter of water; and between about 0.0001 moles and about 0.005 moles of $K_4FeCN_6$ per liter of water, preferably about 0.001 moles per liter of water. Conventional etching solutions such as the ones described in Xia, et al. *Chem. Mater.* 1995, 7, 2332–2337, hereby incorporated by reference, are also useful in practicing the invention.

Preferred etching solutions include: 1 M KOH/0.1 M KCN aqueous solution and 0.1 M $Na_2S_2O_3$/1.0 M KOH/ 0.01 M $K_3Fe(CN)_6$/0.001 M $K_4FeCN_6$ aqueous solution.

The invention is further illustrated by the following non-limiting examples.

EXAMPLE 1

Assays Employing Silver Staining

Capture oligonucleotides (3'-HS(CH$_2$)$_3$-A$_{10}$ATGCTCAACTCT) were prepared and immobilized on a glass substrate as described in WO 98/04740. A target oligonucleotide (5'-TACGAGTTGAGAATCCTGAATGCG-3', concentrations given below in Table 1 for each experiment) was hybridized with the capture of oligonucleotides in 0.3 M NaCl, 10 mM phosphate buffer as described in WO 98/04740. The substrate was rinsed twice with the same buffer solution and immersed in a solution containing gold nanoparticle probes functionalized with target-complementary DNA (5'-HS (CH$_2$)$_6$A$_{10}$CGCATTCAGGAT) (preparation described in WO 98/04740) for 12 hours. Next, the substrate was rinsed copiously with 0.3 M NaNO$_3$ to remove Cl$^-$. The substrate was then developed with silver staining solution (1:1 mixture of Silver Enhancer Solutions A and B, Sigma Chemical Co., # S-5020 and # S-5145) for 3 minutes. Grayscale measurements were made by scanning the silver enhanced substrate on a flatbed scanner (normally used for scanning documents into a computer) linked to a computer loaded with software capable of calculating grayscale measurements (e.g., Adobe Photoshop). The results are presented in Table 1 below.

TABLE 1

| Target DNA Concentration | Mean Grayscale | Standard Deviation |
| --- | --- | --- |
| 101 nM | 47.27 | 2.10 |
| 5 nM | 53.45 | 0.94 |
| 2 nM | 54.56 | 1.17 |
| 1 nM | 59.98 | 1.82 |
| 500 pM | 61.61 | 2.26 |
| 200 pM | 90.06 | 3.71 |
| 100 pM | 99.04 | 2.84 |
| 50 pM | 135.20 | 7.49 |
| 20 pM | 155.39 | 3.66 |
| None (control) | 168.16 | 10.03 |

EXAMPLE 2

Removal of Silver By Chemical Etching

A silver stained DNA chip, such as the one produced in Example 1, was dipped in ferri/ferrocyanide etchant (0.1 M Na$_2$S$_2$O$_3$, 1.0 M KOH, 0.01 M K$_3$Fe(CN)$_6$, 0.001 M K$_4$Fe (CN)$_6$). The silver stain and gold nanoparticles were dissolved (by oxidation) and washed away, leaving a transparent DNA chip. The etching time ranges from a few seconds to a few minutes depending on the amount of silver on the chip. To test the regenerated chip, target DNA, gold probes and silver staining solution were applied to the regenerated chip, successively. The regenerated chip worked as well as a new one. Additionally, the gold nanoparticles hybridized to the regenerated chip could be removed by washing with water or heating above the melting temperature in 0.3 M PBS. These results demonstrate that the chemical etching can remove silver stain without damaging the DNA chip.

EXAMPLE 3

Removal of Silver by Sonication

Silver stain and gold nanoparticles could also be removed by sonication. A silver stained DNA chip, such as the one produced in Example 1, was submersed into a sonicator (Branson model No.2210 sonicator) for 3–5 minutes at room temperature. The sonication process removed the silver metal as well as the gold nanoparticles to produce the regenerated chip. To test the regenerated chip, target DNA, gold probes and silver staining solution were applied to the regenerated chip, successively. The gold nanoparticle signal intensity still maintains above 90% after 3 cycles. These results demonstrate that the sonication process can remove silver stain without substantial damage to the DNA chip.

What we claim:

1. A method for recycling a silver stained DNA detection chip having bound nanoparticles, said method comprising the steps of:
   (a) providing an etching solution;
   (b) contacting the chip with the etching solution for a time sufficient to remove the silver stain; and
   (c) washing the etching solution away from the chip so as to produce a recycled chip for subsequent reuse in a nucleic acid hybridization assay.

2. The method according to claim 1, wherein the etching solution is a cyanide etching solution.

3. The method according to claim 2 wherein the cyanide etching solution comprises:
   0.01 M to 0.5 M $Na_2S_2O_3$;
   0.1 M to 2 MKOH;
   0.001 M to 0.1 M $K_3Fe(CN)_6$; and
   0.0001 M to 0.005 M $K_4Fe(CN)_6$.

4. The method of claim 2 Wherein the cyanide etching solution comprises:
   0.1 M $Na_2S_2O_3$;
   1.0 M KOH; 0.01 M $K_3Fe(CN)_6$; and 0.001 M $K_4Fe(CN)_6$.

5. The method of claim 2 wherein the cyanide etching solution comprises:
   0.005 M to 0.5 M KCN; and
   0.1 to 2 M KOH.

6. The method of claim 2 wherein the cyanide etching solution comprises:
   0.1 M KCN; and
   1.0 MKOH.

7. The method of claims 3 or 5 wherein the cyanide etching solution is applied by dipping the chip in the cyanide etching solution.

8. The method of claims 3 or 5 wherein the cyanide etching solution is applied by spraying the chip with the cyanide etching solution.

9. The method of claims 3 or 5 wherein the cyanide etching solution is removed by washing with water.

10. The method of claims 3 or 5 wherein the cyanide etching solution is applied for between about 1 second and about 10 minutes.

11. The method of claim 1 wherein the silver stained DNA chip has bound nanoparticles.

12. The method of claim 11 wherein the nanoparticles catalyze silver reduction.

13. The method of claim 11 wherein the nanoparticles comprise gold or silver.

14. A method for recycling a silver stained DNA detection chip having bound nanoparticles for subsequent reuse in a nucleic acid hybridization assay, said method comprising subjecting the detection chip to ultrasound waves for a time sufficient to remove the silver stain and to produce a recycled chip for subsequent reuse in a nucleic acid hybridization assay.

15. The method of claim 14, wherein the chip is subjected to ultrasound waves by submersing the chip in a sonicator.

16. The method of claim 15 wherein the chip is submersed in the sonicator for between about 3 minutes and about 5 minutes.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 1
tctcaactcg taaaaaaaaa aa                                              22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 2
tacgagttga gaatcctgaa tgcg                                            24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 3
aaaaaaaaaa cgcattcagg at                                              22
```